US008829024B2

(12) United States Patent
Belanoff et al.

(10) Patent No.: US 8,829,024 B2
(45) Date of Patent: Sep. 9, 2014

(54) COMBINATION STEROID AND GLUCOCORTICOID RECEPTOR ANTAGONIST THERAPY

(75) Inventors: Joe Belanoff, Menlo Park, CA (US); Peter Lockey, Harlow Essex (GB)

(73) Assignee: Corcept Therapeutics, Inc., Menlo Park, CA (US)

(*) Notice: Subject to any disclaimer, the term of this patent is extended or adjusted under 35 U.S.C. 154(b) by 193 days.

(21) Appl. No.: 13/345,242

(22) Filed: Jan. 6, 2012

(65) Prior Publication Data
US 2013/0012486 A1 Jan. 10, 2013

Related U.S. Application Data

(60) Provisional application No. 61/430,786, filed on Jan. 7, 2011, provisional application No. 61/492,440, filed on Jun. 2, 2011.

(51) Int. Cl.
*A61K 31/44* (2006.01)
*A61K 31/415* (2006.01)
*A61K 31/573* (2006.01)
*A61K 45/06* (2006.01)
*A61K 31/437* (2006.01)

(52) U.S. Cl.
CPC ............ *A61K 31/437* (2013.01); *A61K 31/573* (2013.01); *A61K 45/06* (2013.01)
USPC ......................................... 514/293; 514/406

(58) Field of Classification Search
USPC .................................. 514/293, 406
See application file for complete search history.

(56) References Cited

U.S. PATENT DOCUMENTS

| | | | |
|---|---|---|---|
| 7,678,813 B2 | 3/2010 | Clark et al. | |
| 7,790,745 B2 | 9/2010 | Yang et al. | |
| 7,928,237 B2 | 4/2011 | Clark et al. | |
| 8,461,172 B2 | 6/2013 | Clark et al. | |
| 2002/0065259 A1 | 5/2002 | Schatzberg et al. | |
| 2004/0014741 A1 | 1/2004 | Liu et al. | |
| 2007/0281928 A1 | 12/2007 | Clark et al. | |
| 2008/0070950 A1 | 3/2008 | Benjamin et al. | |
| 2009/0286835 A1* | 11/2009 | Bladh et al. | 514/341 |
| 2010/0292477 A1 | 11/2010 | Clark et al. | |
| 2012/0220565 A1 | 8/2012 | Clark et al. | |
| 2013/0225633 A1 | 8/2013 | Hunt et al. | |

FOREIGN PATENT DOCUMENTS

| | | |
|---|---|---|
| EP | 0145121 A2 | 6/1985 |
| EP | 0375210 A1 | 6/1990 |
| JP | 9-505030 A | 5/1997 |
| JP | 2002-506032 A | 2/2002 |
| JP | 2002-544271 A | 12/2002 |
| WO | 95/04734 A1 | 2/1995 |
| WO | 99/45925 A1 | 9/1999 |
| WO | 00/69846 A1 | 11/2000 |
| WO | 03/015692 A2 | 2/2003 |
| WO | 03/061651 A1 | 7/2003 |
| WO | 2005/087769 A1 | 9/2005 |
| WO | 2010/132445 A1 | 11/2010 |
| WO | 2012/094618 A1 | 7/2012 |

OTHER PUBLICATIONS

Dirks NL, Li S, Huth B, Hochhaus G, Yates CR, Meibohm B. Transrepression and transactivation potencies of inhaled glucocorticoids. Pharmazie. Dec. 2008;63(12):893-8.*
Heck S, Kullmann M, Gast A, Ponta H, Rahmsdorf HJ, Herrlich P, Cato AC. A distinct modulating domain in glucocorticoid receptor monomers in the repression of activity of the transcription factor AP-1. EMBO J. Sep. 1, 1994;13(17):4087-95.*
Clark RD, Ray NC, Williams K, Blaney P, Ward S, Crackett PH, Hurley C, Dyke HJ, Clark DE, Lockey P, Devos R, Wong M, Porres SS, Bright CP, Jenkins RE, Belanoff J. 1H-Pyrazolo[3,4-g]hexahydro-isoquinolines as selective glucocorticoid receptor antagonists with high functional activity. Bioorg Med Chem Lett. Feb. 15, 2008;18(4):1312-7.*
Belanoff, et al., "Selective glucocorticoid receptor (type II) antagonist prevents and reverses olanzapine-induced weight gain," Diabetes, Obesity & Metabolism, vol. 12(6), pp. 545-547 (2010).
Clark et al., "1H-Pyrazolo[3,4-g]hexahydro-isoquinolines as selective glucocorticoid receptor antagonists with high functional activity," Bioorganic & Medical Chemistry Letters, 18, pp. 1312-1317 (2008).
De Bosscher, et al., "Classic glucocorticoids versus non-steroidal glucocorticoid receptor modulators: Survival of the fittest regulator of the immune system?" Brain, Behavior and Immunity, vol. 24(7), pp. 1035-1042 (2010).
Schacke, et al., "Mechanisms involved in the side effects of glucocorticoids," Pharmacology & Therapeutics, vol. 96(1), pp. 23-43 (2002).
Schacke, et al., "Selective glucocorticoid receptor agonists (SEGRAs): Novel ligands with an improved therapeutic index", Molecular and Cellular Endocrinology, vol. 275(1-2), pp. 109-117 (2007).
Wayne Genck. 2004, Chemical Processing.com.
European Search Report for European Application No. 12732354.1, dated Nov. 7, 2013, 13 pages.
JP Office Action from JP Application No. 2007-503030, dated Feb. 23, 2011, 8 pages.
International Search Report dated Jun. 15, 2005, issued in related International Application No. PCT/US2005/008049, filed Mar. 9, 2005.
International Search Report and Written Opinion, dated Jul. 9, 2010, issued in related International Patent Application No. PCT/US2010/034382, filed May 11, 2010.

(Continued)

*Primary Examiner* — Paul Zarek
(74) *Attorney, Agent, or Firm* — Kilpatrick Townsend & Stockton LLP

(57) ABSTRACT

The present invention provides compositions of an anti-inflammatory glucocorticosteroid and a glucocorticoid receptor (GR) modulator useful for inhibiting glucocorticoid receptor induced transactivation without substantially inhibiting glucocorticoid receptor induced transrepression. Also provided are methods of treating a disorder or condition and reducing the side effects of glucocorticosteroid treatment, using the compositions of the present invention.

8 Claims, 2 Drawing Sheets

(56) References Cited

OTHER PUBLICATIONS

International Search Report and Written Opinion dated May 4, 2012, issued in related International Patent Appln. No. PCT/US12/20521, filed Jan. 6, 2012.

International Search Report and Written Opinion dated Jan. 30, 2012, issued in related International Patent Appln. No. PCT/US11/49408, filed Aug. 26, 2011.

International Search Report and Written Opinion dated Jun. 17, 2013, issued in related International Patent Appln. No. PCT/US13/27720 filed Feb. 26, 2013.

Communication of European publication number and information on the application of Article 67(3) EPC for European Application No. 1273254.1 dated Oct. 16, 2013.

* cited by examiner

COMBINATION STEROID AND GLUCOCORTICOID RECEPTOR ANTAGONIST THERAPY

CROSS-REFERENCES TO RELATED APPLICATIONS

This application claims priority to U.S. Provisional Application Nos. 61/430,786, filed Jan. 7, 2011, and 61/492,440, filed Jun. 2, 2011, which are incorporated in their entirety herein for all purposes.

BACKGROUND OF THE INVENTION

In most species, including man, the physiological glucocorticosteroid is cortisol (hydrocortisone). Glucocorticosteroids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a glucocorticosteroid and acts by binding to an intracellular, glucocorticoid receptor (GR). In man, glucocorticoid receptors are present in two forms: a ligand-binding GR-alpha of 777 amino acids; and a GR-beta isoform which lacks the 50 carboxy terminal amino acids. Since these include the ligand binding domain, GR-beta is unable to bind ligand, is constitutively localized in the nucleus, and is transcriptionally inactive. The glucocorticoid receptor, GR, is also known as the glucocorticoid receptor II, or GRII.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

In addition to cortisol, the biological effects of other glucocorticosteroids can be modulated at the GR level using receptor modulators, such as agonists, partial agonists and antagonists. When administered to subjects in need thereof, glucocorticosteroids can provide both intended therapeutic effects as well as undesirable side effects. The beneficial therapeutic effects are normally considered to be the result of GR induced gene transrepression, while most of the undesirable side effects are associated with GR induced gene transactivation. What is needed in the art are new compositions and methods for ameliorating the negative side effects of glucocorticosteroids by inhibiting chronic glucocorticoid receptor induced transactivation while not significantly reducing the intended therapeutic effects afforded by glucocorticoid receptor induced transrepression. Surprisingly, the present invention meets these and other needs.

BRIEF SUMMARY OF THE INVENTION

In a first embodiment, the present invention provides a composition that includes an anti-inflammatory glucocorticosteroid and a glucocorticoid receptor (GR) modulator of Formula I:

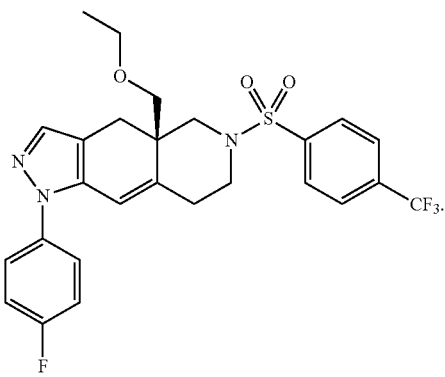 [SMILES: CCOC[C@]12Cc3cnn(-c4ccc(F)cc4)c3C=C1CCN(S(=O)(=O)c1ccc(C(F)(F)F)cc1)C2]

In a second embodiment, the present invention provides a method of inhibiting glucocorticoid receptor (GR) induced transactivation without substantially inhibiting GR-induced transrepression, wherein the method includes contacting a GR with a composition having an anti-inflammatory glucocorticosteroid and a GR modulator of Formula I, in an amount sufficient to inhibit GR induced transactivation without substantially inhibiting GR-induced transrepression.

In a third embodiment, the present invention provides a method of treating a disorder or condition, wherein the method includes administering to a subject in need thereof, a therapeutically effective amount of a composition having an anti-inflammatory glucocorticosteroid and a glucocorticoid receptor (GR) modulator of Formula I, thereby treating the disorder or condition.

In a fourth embodiment, the present invention provides a method of reducing the side effects of glucocorticosteroid treatment, including administering to a subject in need thereof, a therapeutically effective amount of a composition having an anti-inflammatory glucocorticosteroid and a glucocorticoid receptor (GR) modulator of Formula I, thereby reducing the side effects of glucocorticosteroid treatment.

BRIEF DESCRIPTION OF THE DRAWINGS

FIG. 1a shows that dexamethasone causes potent transrepression at nanomolar concentrations (the inhibition of LPS activated TNFα release) whereas CORT-108297 alone does not cause transrepression until micromolar concentrations are used (circles). FIG. 1b shows that while mifepristone completely inhibits dexamethasone induced transrepression (squares), CORT-108297 only partially inhibits dexamethasone induced transrepression, and a higher concentration is required (circles).

FIG. 2b shows that CORT-108297 is an antagonist of GR induced transactivation because CORT-108297 reverses dexamethasone induction of the expression of tyrosine amino transferase. FIG. 2b shows both mifepristone and CORT-108297 inhibiting dexamethasone induced transactivation (shown by inhibiting the increased expression of tyrosine amino transferase).

DETAILED DESCRIPTION OF THE INVENTION

I. General

Figure 1:
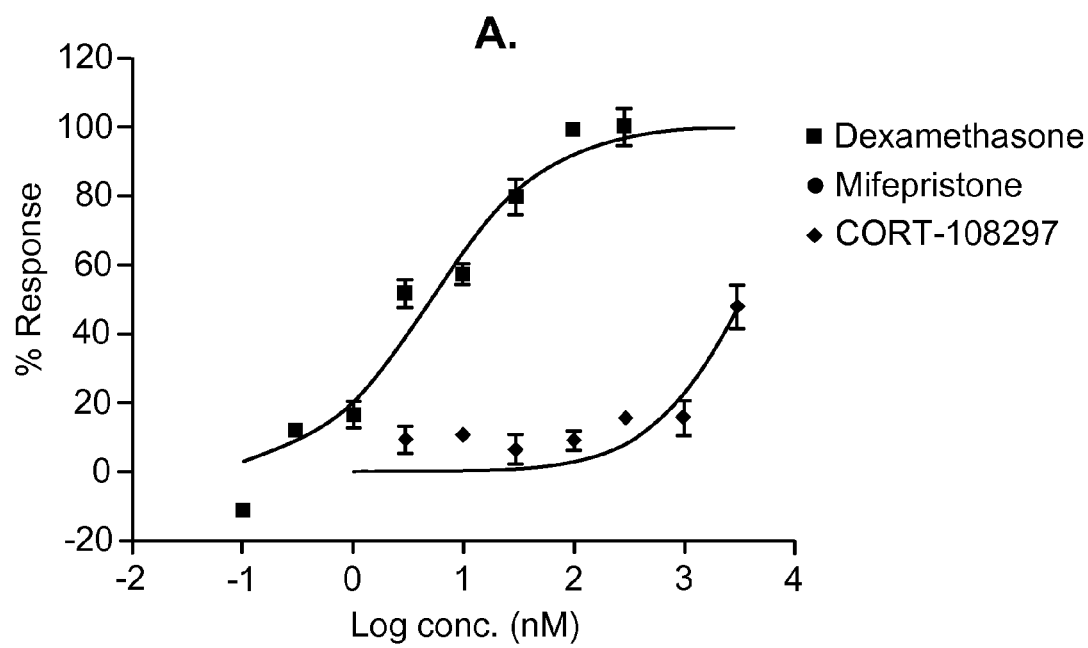
FIG. 1 shows that CORT-108297 does not substantially inhibit dexamethasone induced transrepression.
Figure 1:
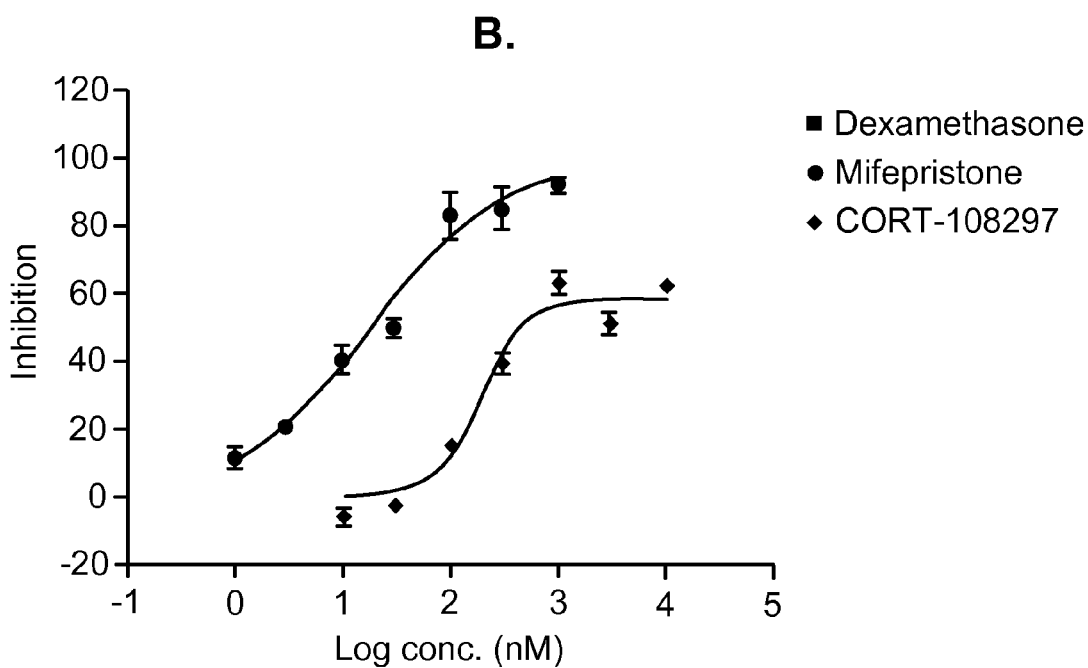

The present invention provides a composition of an anti-inflammatory glucocorticosteroid and a glucocorticoid receptor (GR) modulator that provides the beneficial properties of glucocorticosteroid treatment while reducing the side effects of glucocorticosteroid treatment, such as weight gain and increased blood pressure. This beneficial property is afforded by inhibition of GR induced transactivation by the GR modulator without substantial inhibition of GR induced transrepression by the GR modulator.

II. Definitions

"Salt" refers to acid or base salts of the anti-inflammatory glucocorticosteroids used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium(methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomers" refers to compounds having the same number and kind of atoms, and hence the same molecular weight, but differing in respect to the structural arrangement or configuration of the atoms.

"Tautomer," refers to one of two or more structural isomers which exist in equilibrium and which are readily converted from one isomeric form to another.

"Glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

"Anti-inflammatory glucocorticosteroid" refers to a class of steroid hormones that bind to the glucocorticoid receptor and reduce inflammation. Examples of anti-inflammatory glucocorticosteroids include, but are not limited to, cortisol (the physiological glucocorticoid) as well as alclometasone, betamethasone, budesonide, ciclesonide, clobetasol, clocortolone, deprodone, desonide, dexamethasone, difluprednate, flunisolide, fluocinolone, fluticasone, halcinonide, halometasone, halopredone, hydrocortisone, loteprednol, methylprednisolone, mometasone, naflocort, oxazacort, paramethasone, prednicarbate, prednisolone, prednisone, triamcinolone, trimexolone, and ulobetasol. Glucocorticosteroids are part of a class of compounds called corticosteroids that also includes mineralocorticosteroids. The anti-inflammatory glucocorticosteroids of the present invention bind to glucocorticoid receptor and not to the mineralocorticoid receptor, also known as the glucocorticoid receptor I (GRI).

"GR induced transactivation" refers to gene expression induced by binding of a GR agonist to a glucocorticoid receptor. For example, GR induced transactivation can occur when an anti-inflammatory glucocorticosteroid, such as dexamethasone, binds to a glucocorticoid receptor. In the present invention, inhibition of GR induced transactivation occurs with at least 25% inhibition of the GR induced transactivation activity.

"GR induced transrepression" refers to inhibition of gene expression induced by binding of a GR agonist to a glucocorticoid receptor. The GR modulators of the present invention have minimal effect on GR induced transrepression. In the present invention, substantially not inhibiting GR-induced transrepression is when GR-induced transrepression activity in the presence of the GR modulator is at least 50% of the activity observed in the absence of the GR modulator.

"Patient" or "subject in need thereof" refers to a living organism suffering from or prone to a condition that can be treated by administration of a pharmaceutical composition as provided herein. Non-limiting examples include humans, other mammals and other non-mammalian animals.

"Therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"GR modulator" refers to compounds that agonize and/or antagonize the glucocorticoid receptor and are defined as the compound of Formula I below.

"Disorder" or "condition" refer to a state of being or health status of a patient or subject capable of being treated with the glucocorticoid receptor modulator of the present invention. Examples of disorders or conditions include, but are not limited to, obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches.

III. Compositions of an Anti-Inflammatory Glucocorticosteroid and a GR Modulator The present invention provides a series of anti-inflammatory glucocorticosteroids and glucocorticoid receptor (GR) modulators that are useful for inhibiting GR induced transactivation without substantially reducing GR induced transrepression. Anti-inflammatory glucocorticosteroids suitable for use with the present invention are listed below. GR modulators suitable for use with the present invention have the structure of Formula I.

In some embodiments, the present invention provides a composition including an anti-inflammatory glucocorticosteroid and a glucocorticoid receptor (GR) modulator of Formula I:

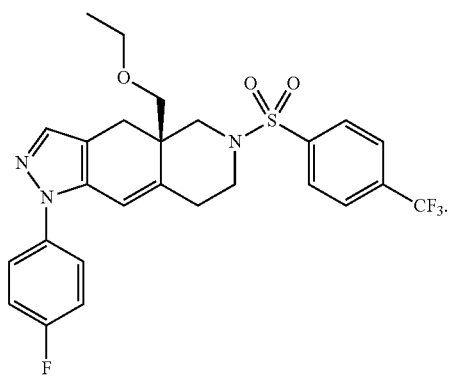 [SMILES: CCOC[C@]12Cc3cnn(-c4ccc(F)cc4)c3C=C1CCN(S(=O)(=O)c1ccc(C(F)(F)F)cc1)C2]

In some embodiments, the compositions can also include salts and isomers of the anti-inflammatory glucocorticosteroids of the present invention.

GR Modulators

In some embodiments, the present invention provides a composition including an anti-inflammatory glucocorticosteroid and a GR modulator of Formula I.

It will be apparent to one skilled in the art that certain compounds of this invention may exist in tautomeric forms, all such tautomeric forms of the compounds being within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon, are within the scope of this invention. All isotopic variations of the compounds of the present invention, whether radioactive or not, are encompassed within the scope of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Synthesis of GR Modulators of Formula I

The compounds of the invention can be synthesized by a variety of methods known to one of skill in the art (see *Comprehensive Organic Transformations* Richard C. Larock, 1989) or by an appropriate combination of generally well known synthetic methods.

The GR modulators of the present invention can be synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. Exemplary syntheses of the compounds of Formula I can be found in U.S. patent application Ser. No. 10/591,884, now U.S. Pat. No. 7,928,237, and in *Bioorganic & Medicinal Chemistry Letters* 18(4), 1312, 2008.

Scheme 1.

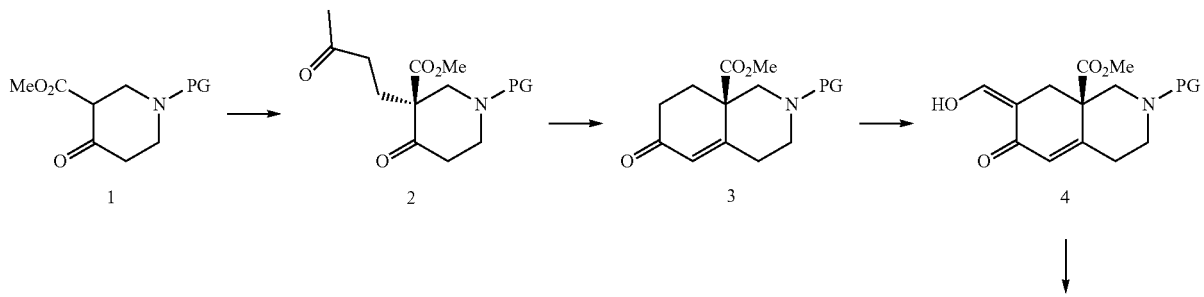

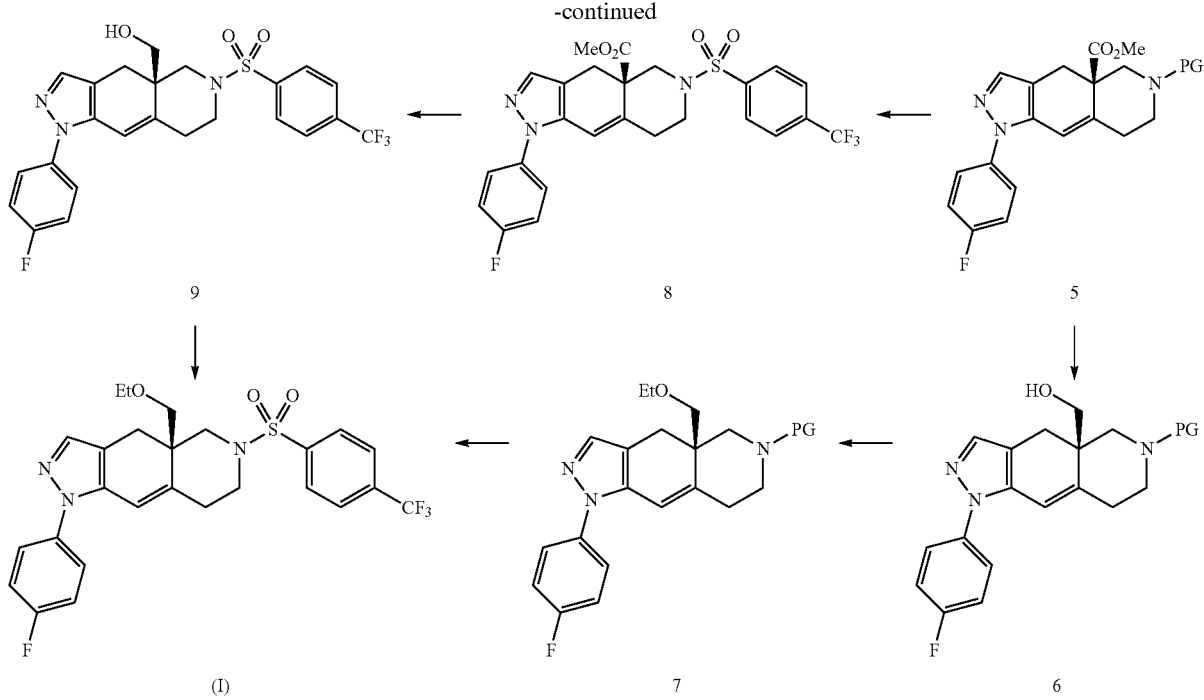

Compounds of Formula (I) are prepared as described in Scheme 1. In Scheme 1, PG represents a suitable protecting group, such as BOC or benzyl, to facilitate the synthesis. Keto-ester 1 is converted directly to enone 3 by a Robinson annelation reaction involving treatment of 1 with a base (e.g. potassium or sodium alkoxides) in an alcohol solvent (e.g. methanol, ethanol, or tert-butanol) followed by addition of methylvinyl ketone (MVK). The reaction is typically carried out at 0-25° C.

Alternatively, compound 3 can be prepared in optically active form. The suitably N-protected piperidone-2-carboxylic acid ester 1 is heated with an optically active nitrogen-containing base (as described in J. Med. Chem. 39: 2302 (1996)) such as (R)-(+)-α-methylbenzylamine or (S)-2-amino-N,N-diethyl-3-methyl-butyramide, in a suitable solvent (such as toluene, benzene or dioxane) under dehydrating conditions (concentrated HCl, molecular sieves or Dean-Stark trap). The intermediate enamine is then treated with methylvinyl ketone in an apolar solvent such as acetone in the presence of copper$^{II}$ acetate to afford the optically active methylvinyl ketone adduct 2.

Optically active ketone 2 is converted to enone 3 by treatment with a base (e.g. potassium or sodium alkoxides) in an alcohol solvent (e.g. methanol, ethanol, or tert-butanol) or by addition of a nitrogen-containing base such as pyrrolidine, piperidine or morpholine in an aprotic solvent (e.g. benzene, toluene or dioxane).

Treatment of ketones 3 with a formylating agent such as ethyl formate or trifluoroethyl formate, as described for example in Organic Letters, 1 (7), 989, (1999), in the presence of a base such as sodium methoxide, LDA or sodium hydride in an aprotic solvent such as toluene affords hydroxymethylene derivatives 4. Treatment of 4 with an aryl hydrazine in an alcohol solvent or acetic acid with heating to the reflux temperature of the mixture affords pyrazoles 5.

Alcohols 6 are prepared by treatment of ester 5 with a reducing agent such as DIBAL-H, LiAlH$_4$ or RED-AL in an inert solvent such as THF, benzene or toluene.

Alcohols 6 are converted into ether derivatives 7 by treatment with a base (e.g. sodium hydride) in an aprotic solvent (e.g. tetrahydrofuran, N,N-dimethylformamide) followed by addition of a substituted or unsubstituted alkyl halide. Ethers 7 are converted into compounds of Formula (I) by removal of the protecting group followed by reaction of the resultant unprotected amine with an appropriate sulfonyl chloride. The protecting group can be removed using any method known to those skilled in the art, such as treatment with a chloroformate and subsequent hydrolysis to remove a benzyl group or treatment with an appropriate acid to remove a Boc group. Sulfonylation can be accomplished using standard conditions known to those skilled the art, such as reaction with an appropriate sulfonyl chloride in an inert solvent (such as toluene, dichloromethane, 1,2-dichloroethane or dioxane) in the presence of a base such as triethylamine.

Compounds of Formula (I) can also be prepared as shown in Scheme I by carrying out the synthetic steps in a different order. Removal of the protecting group from compound 5 is accomplished under standard conditions, such as removal of a benzyl group by treatment with a chloroformate and subsequent hydrolysis. Suitable chloroformates include methyl chloroformate, ethyl chloroformate and α-chloroethyl chloroformate. The unprotected amine can then be reacted with an appropriate sulfonyl halide in an inert solvent (e.g. toluene, dichloromethane, 1,2-dichloroethane or dioxane) in the presence of a base such as triethylamine to provide sulfonamide 8. Reduction of the ester to the corresponding alcohol 9 and subsequent conversion to an ether of Formula (I) can be carried out as described above for the conversion of compound 5 to compounds 6 and 7.

Anti-Inflammatory Glucocorticosteroids

Anti-inflammatory glucocorticosteroids suitable for use with the present invention include those glucocorticosteroids that bind GR and include, but are not limited to, alclometasone, alclometasone dipropioate, beclometasone, beclometasone dipropionate, betamethasone, betamethasone butyrate proprionate, betamethasone dipropionate, betamethasone valerate, budesonide, ciclesonide, clobetasol, clobetasol propionate, clocortolone, clocortolone pivalate, cortexolone, cortisol, cortisporin, cortivazol, deflazacort, deprodone, deprodone propionate, desonide, dexamethasone, dexamethasone acetate, dexamethasone cipecilate, dexamethasone palmitate, difluprednate, fludroxycortide, flunisolide, fluocinolone, fluocinolone acetonide, fluocinonide, fluocortolone, fluorometholone, fluticasone, fluticasone propionate, fluticasone furoate, halcinonide, halometasone, halopredone, halopredone acetate, hydrocortisone, hydrocortisone 17-butyrate, hydrocortisone aceponate, hydrocortisone acetate, hydrocortisone probutate, hydrocortisone sodium succinate, loteprednol, loteprednol etabonate, meprednisone, methylprednisolone, methylprednisolone aceponate, methylprednisolone suleptanate, mometasone, mometasone furoate, naflocort, 19-nordeoxycorticosterone, 19-norprogesterone, otobiotic, oxazacort, paramethasone, prednicarbate, prednisolone, prednisolone farnesylate, prednisone, prednisone sodium phosphate, prednylidene, proctosedyl, rimexolone, tobradex, triamcinolone, triamcinolone hexacetonide, trimexolone, ulobetasol, ulobetasol propionate, 11β-(4-dimethylaminoethoxyphenyl)-17α-propynyl-17β-hydroxy-4,9estradien-3-one (RU009), 17β-hydroxy-17α-19-(4-methylphenyl)androsta-4,9(11)-dien-3-one (RU044), and the salt and esters forms thereof.

Additional anti-inflammatory glucocorticosteroids suitable for use with the present invention include, but are not limited to, a naturally occurring or synthetic steroid glucocorticoid which can be derived from cholesterol and is characterized by a hydrogenated cyclopentanoperhydrophenanthrene ring system. Suitable glucocorticosteroids also include, but are not limited to, 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-acetoxypregnenolone; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alphafluoroprednisolone; 6-alpha-methylprednisolone; 6-alpha-methylprednisolone-21-acetate; 6-alpha-methylprednisolone 21-hemisuccinate sodium salt, 6-betahydroxy cortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclomethasone dipropionate; algestone; alphaderm; amadinone; amcinonide; anagestone; androstenedione; anecortave acetate; beclomethasone; beclomethasone dipropionate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; ciclesonide; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortivazol; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; difluprednate; dihydroelatericin a; domoprednate; doxibetasol; ecdysone; ecdysterone; emoxolone; endrysone; enoxolone; fluazacort; flucinolone; flucloronide; fludrocortisone; fludrocortisone acetate; flugestone; flumethasone; flumethasone pivalate; flumoxonide; flunisolide; fluocinolone; fluocinolone acetonide; fluocinonide; fluocortin butyl; 9-fluorocortisone; fluocortolone; fluorohydroxyandrostenedione; fluorometholone; fluorometholone acetate; fluoxymesterone; fluperolone acetate; fluprednidene; fluprednisolone; flurandrenolide; fluticasone; fluticasone propionate; formebolone; formestane; formocortal; gestonorone; glyderinine; halcinonide; halobetasol propionate; halometasone; halopredone; haloprogesterone; hydrocortamate; hydrocortiosone cypionate; hydrocortisone; hydrocortisone; 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; loteprednol etabonate; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednicarbate; prednisolamate; prednisolone; prednisolone 21-diethylaminoacetate; prednisolone 21-hemisuccinate; prednisolone acetate; prednisolone farnesylate; prednisolone hemisuccinate; prednisolone-21 (beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone benetonide; triamcinolone diacetate; triamcinolone hexacetonide; trimegestone; turkesterone; and wortmannin.

Additional anti-inflammatory glucocorticosteroids suitable for use with the present invention include, but are not limited to, alclometasone, beclometasone, betamethasone, budesonide, ciclesonide, clobetasol, clocortolone, cortexolone, cortisol, cortisporin, cortivazol, deflazacort, deprodone, desonide, dexamethasone, difluprednate, fludroxycortide, flunisolide, fluocinolone, fluocinonide, fluocortolone, fluorometholone, fluticasone, halcinonide, halometasone, halopredone, hydrocortisone, loteprednol, meprednisone, methylprednisolone, mometasone, naflocort, 19-nordeoxycorticosterone, 19-norprogesterone, otobiotic, oxazacort, paramethasone, prednicarbate, prednisolone, prednisone, prednylidene, proctosedyl, rimexolone, tobradex, triamcinolone, trimexolone, ulobetasol, 11β-(4-dimethylaminoethoxyphenyl)-17α-propynyl-17β-hydroxy-4, 9estradien-3-one (RU009), and 17β-hydroxy-17α-19-(4-methylphenyl)androsta-4,9(11)-dien-3-one (RU044).

The anti-inflammatory glucocorticosteroids of the present invention also include the salts, hydrates, solvates and prodrug forms. The anti-inflammatory glucocorticosteroids of the present invention also include the isomers and metabolites of those described above.

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

The neutral forms of the anti-inflammatory glucocorticosteroids can be regenerated by contacting the salt with a base or acid and isolating the parent anti-inflammatory glucocorticosteroid in the conventional manner. The parent form of the anti-inflammatory glucocorticosteroid differs from the various salt forms in certain physical properties, such as solubility in polar solvents, but otherwise the salts are equivalent to the parent form of the compound for the purposes of the present invention.

Certain anti-inflammatory glucocorticosteroids of the present invention can exist in unsolvated forms as well as solvated forms, including hydrated forms. In general, the solvated forms are equivalent to unsolvated forms and are encompassed within the scope of the present invention. Certain anti-inflammatory glucocorticosteroids of the present invention may exist in multiple crystalline or amorphous forms. In general, all physical forms are equivalent for the uses contemplated by the present invention and are intended to be within the scope of the present invention.

Certain anti-inflammatory glucocorticosteroids of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The anti-inflammatory glucocorticosteroids of the present invention do not include those which are known in art to be too unstable to synthesize and/or isolate. The present invention is meant to include anti-inflammatory glucocorticosteroids in racemic and optically pure forms. Optically active (R)- and (S)-, or (D)- and (L)-isomers may be prepared using chiral synthons or chiral reagents, or resolved using conventional techniques.

The present invention also provides anti-inflammatory glucocorticosteroids which are in a prodrug form. Prodrugs of the anti-inflammatory glucocorticosteroids described herein are those anti-inflammatory glucocorticosteroids that readily undergo chemical changes under physiological conditions to provide the compounds of the present invention. Additionally, prodrugs can be converted to the anti-inflammatory glucocorticosteroids of the present invention by chemical or biochemical methods in an ex vivo environment. For example, prodrugs can be slowly converted to the anti-inflammatory glucocorticosteroids of the present invention when placed in a transdermal patch reservoir with a suitable enzyme or chemical reagent.

IV. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the anti-inflammatory glucocorticosteroid and/or the GR modulator of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the anti-inflammatory glucocorticosteroid and/or the GR modulator of Formula I.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the anti-inflammatory glucocorticosteroid and/or the GR modulator of Formula I mixed with a filler or binders such as lactose or starches, lubricants such as talc or magnesium stearate, and, optionally, stabilizers. In soft capsules, the anti-inflammatory glucocorticosteroid and/or the GR modulator of Formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the anti-inflammatory glucocorticosteroid and/or the GR modulator of Formula I are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the anti-inflammatory glucocorticosteroid and/or the GR modulator of Formula I in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the anti-inflammatory glucocorticosteroid and/or the GR modulator of Formula I in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

V. Administration

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the anti-inflammatory glucocorticosteroid and/or the GR modulator of Formula I. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The anti-inflammatory glucocorticosteroid of the present invention and the GR modulator of Formula I can be co-administered or administered separately. Co-administration includes administering the anti-inflammatory glucocorticosteroid within 0.5, 1, 2, 4, 6, 8, 10, 12, 16, 20, or 24 hours of the GR modulator of Formula I. Co-administration also includes administering the anti-inflammatory glucocorticosteroid and the GR modulator of Formula I simultaneously, approximately simultaneously (e.g., within about 1, 5, 10, 15, 20, or 30 minutes of each other), or sequentially in any order. Moreover, the anti-inflammatory glucocorticosteroid and the GR modulator of Formula I can each be administered once a day, or two, three, or more times per day so as to provide the preferred dosage level per day.

In some embodiments, co-administration can be accomplished by co-formulation, i.e., preparing a single pharmaceutical composition including both the anti-inflammatory glucocorticosteroid and the GR modulator of Formula I. In other embodiments, the anti-inflammatory glucocorticosteroid and the GR modulator of Formula I can be formulated separately.

The anti-inflammatory glucocorticosteroid can be present in any suitable amount, and can depend on various factors including, but not limited to, weight and age of the subject, state of the disease, etc. Suitable dosage ranges for the anti-inflammatory glucocorticosteroid in combination with the GR modulator of Formula I, include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the anti-inflammatory glucocorticosteroid in combination with the GR modulator of Formula I, include about 1 mg, 5, 10, 20, 30, 40, 50, 60, 70, 80, 90, 100, 200, 300, 400, 500, 600, 700, 800, 900 or 1000 mg.

Similarly, the GR modulator of Formula I can be present in combination with the anti-inflammatory glucocorticosteroid in any amount suitable to not substantially inhibit GR induced transrepression activity resulting from the anti-inflammatory glucocorticosteroid while substantially inhibiting GR induced transactivation. The amount of GR modulator of Formula I can depend on various factors including, but not limited to, weight and age of the subject, state of the disease, etc. Suitable dosage ranges for the GR modulator of Formula I in combination with the anti-inflammatory glucocorticosteroid, include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the GR modulator of Formula I in combination with the anti-inflammatory glucocorticosteroid, include, but are not limited to, about 1 mg, 5, 10, 20, 30, 40, 50, 60, 70, 80, 90, 100, 200, 300, 400, 500, 600, 700, 800, 900 or about 1000 mg.

The anti-inflammatory glucocorticosteroid of the present invention and the GR modulator of Formula I can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The anti-inflammatory glucocorticosteroid of the present invention and the GR modulator of Formula I can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the anti-inflammatory glucocorticosteroid and the GR modulator of Formula I are suitable in the compositions and methods of the present invention.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

VI. Methods of Treating and Reducing Steroid Side Effects

The compounds and compositions of the present invention are useful in a variety of methods such as treating a disorder or condition and reducing the side effects of glucocorticosteroid treatment.

In some embodiments, the present invention provides a method of inhibiting glucocorticoid receptor (GR) induced transactivation without substantially inhibiting GR-induced transrepression, wherein the method includes contacting a GR with a composition including an anti-inflammatory glucocorticosteroid and a GR modulator of Formula I:

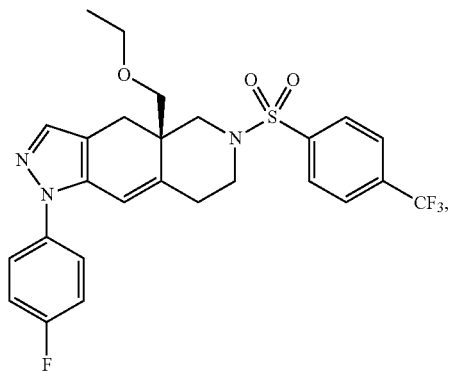 [SMILES: CCOC[C@]12Cc3cnn(-c4ccc(F)cc4)c3C=C1CCN(S(=O)(=O)c1ccc(C(F)(F)F)cc1)C2]

in an amount sufficient to inhibit GR induced transactivation without substantially inhibiting GR-induced transrepression.

The GR modulators of the present invention inhibit transactivation when GR induced transactivation of gene expression is reduced by at least about 50%, relative to the level of gene expression observed in the absence of the GR modulator. For example, GR induced transactivation can be inhibited by at least about 50, 55, 60, 65, 70, 75, 80, 85, 90, 95, 96, 97, 98 or 99%. In some embodiments, glucocorticoid receptor induced transactivation is inhibited by at least about 50%. In other embodiments, glucocorticoid receptor induced transactivation is inhibited by at least about 65%. In some other embodiments, glucocorticoid receptor induced transactivation is inhibited by at least about 75%. In still other embodiments, glucocorticoid receptor induced transactivation is inhibited by at least about 85%. In yet other embodiments, glucocorticoid receptor induced transactivation is inhibited by at least about 95%.

The GR modulators of the present invention, while inhibiting GR induced transactivation, do not substantially inhibit GR-induced transrepression activity. For example, GR-induced transrepression is considered not substantially inhibited when, in the presence of the composition of the present invention, the GR-induced transrepression activity is inhibited by less than about 75%, relative to the level of GR-induced transrepression activity in the absence of the GR modulator of the present invention. GR-induced transrepression is also considered not substantially inhibited when the GR-induced transrepression activity is inhibited by less than about 70, 60, 50, 40, 35, 30, 25, 20, 15, 10, 5, 4, 3, 2 or 1%, relative to the level of GR-induced transrepression activity in the absence of the GR modulator of the present invention. In some embodiments, GR-induced transrepression activity is inhibited by less than about 50%. In other embodiments, GR-induced transrepression activity is inhibited by less than about 25%. In some other embodiments, GR-induced transrepression activity is inhibited by less than about 10%.

In other embodiments, the ratio of percent inhibition of GR induced transactivation inhibition to percent inhibition of GR-induced transrepression inhibition can be from about 1000 to 1. For example, the ratio of percent inhibition of GR induced transactivation inhibition to percent inhibition of GR-induced transrepression inhibition can be about 1000, 500, 100, 90, 80, 70, 60, 50, 40, 30, 25, 20, 15, 10, 5, 4, 3, 2, or 1.

In some other embodiments, the GR induced transactivation is caused by the anti-inflammatory glucocorticosteroid described above.

In some embodiments, the present invention provides a method of treating a disorder or condition, including administering to a subject in need thereof, a therapeutically effective amount of a composition including an anti-inflammatory glucocorticosteroid and a GR modulator of Formula I. In some other embodiments, the anti-inflammatory glucocorticosteroid and GR modulator of the present invention modulate the activity of a GR. The diseases and conditions include, among other, inflammatory conditions and autoimmune diseases. In some embodiments, the disorder or condition can be glaucoma, inflammatory diseases, rheumatoid arthritis, asthma and rhinitis, allergies and autoimmune diseases. Representative autoimmune disease include, but are not limited to, obstructive airways disease, including conditions such as COPD, asthma (e.g intrinsic asthma, extrinsic asthma, dust asthma, infantile asthma), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g. Crohn's disease and ulcerative colitis), atherosclerosis and amyotrophic lateral sclerosis. Other autoimmune diseases include tissue and organ transplants, and allergies.

In some embodiments, the present invention provides a method of reducing the side effects of glucocorticosteroid treatment, including administering to a subject in need thereof, a therapeutically effective amount of a composition including an anti-inflammatory glucocorticosteroid and a GR modulator having the structure of Formula I. In some embodiments, the side effects of glucocorticosteroid treatment can be weight gain, glaucoma, fluid retention, increased blood pressure, mood swings, cataracts, high blood sugar, diabetes, infection, loss of calcium from bones, osteoporosis, or menstrual irregularities. Additional side effects include muscle wasting, fat redistribution, growth retardation and cushingoid appearance.

Assays to Identify GR Modulators

Figure 2:
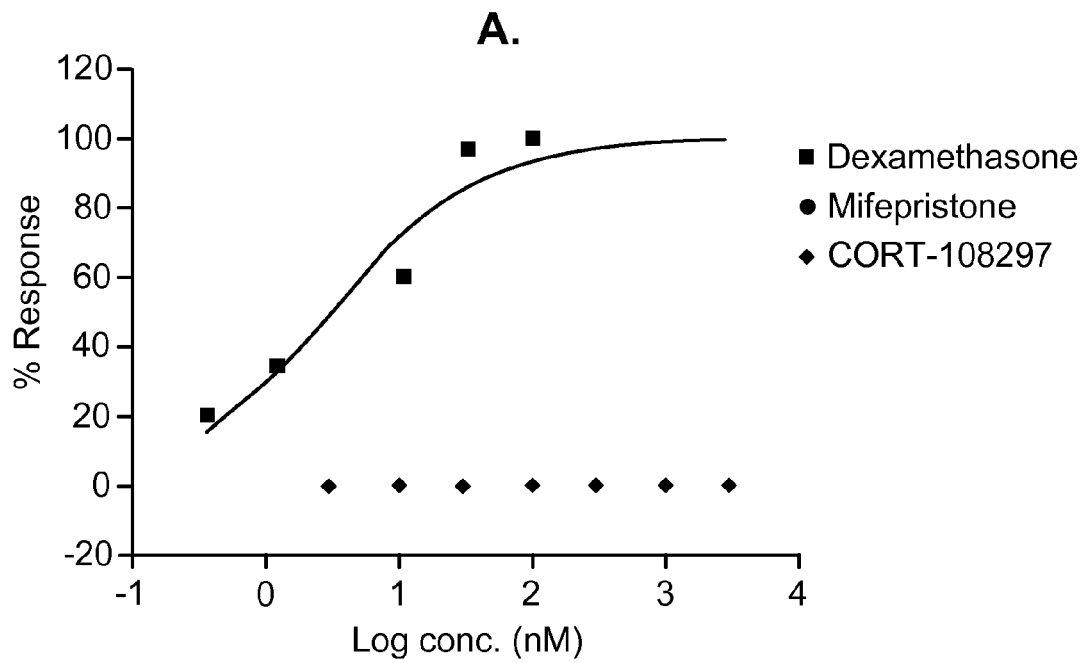
FIG. 2 shows that CORT-108297 substantially inhibits dexamethasone induced transactivation.

GR modulators of the present invention that inhibit GR induced transactivation can be identified by measuring the amount of tyrosine amino transferase expressed in the presence of the GR induced transactivation in a cell model (human liver hepatocytes). GR modulators useful in the present invention are those that inhibit GR induced transactivation by at least about 50%. As demonstrated in FIG. 2A, dexamethasone causes a dose dependent increase in the expression of tyrosine amino transferase, with maximal increase observed at about 100 nM concentration of dexamethasone. In contrast, and as demonstrated in FIG. 2A, the expression of tyrosine amino transferase does not increase above about 0% for all the concentrations of CORT-108297 assayed, demonstrating that the GR modulators of the present invention do not cause GR induced transactivation. FIG. 2B demonstrates that CORT-108297 inhibits the dexamethasone induced transactivation Moreover, the GR modulators of the present invention do not inhibit the GR-induced transrepression activity by more than about 50%. Specifically, the compositions of the present invention do not substantially inhibit the GR-induced transrepression activity of dexamethasone with regard to LPS activated TNFα release (NFκB responsive gene). Using a cell-based model (human peripheral blood mononuclear cells), dexamethasone was administered to the cells and the release of TNFα was measured. After addition of the GR modulator of the present invention, the release of TNFα was again measured and compared to the amount released in the absence of the GR modulator. FIG. 1A shows that dexamethasone is able to inhibit the release of TNFα at nanomolar concentrations. FIG. 1B shows that while mifepristone substantially blocks the inhibition of the release of TNFα, a GR modulator of the present invention does not substantially block the effect of dexamethasone, and thus, does not substantially inhibit GR-induced transrepression.

VII. Examples

Example 1

Glucocorticosteroid Transactivation Assay

This example demonstrates that the compositions of the present invention inhibit glucocorticosteroid induced transactivation. In this example, dexamethasone induces the expression of tyrosine amino transferase by transactivation. Typically, glucocorticosteroids, such as the synthetic dexamethasone, bind the ligand-binding domain of the glucocorticoid receptor (GR) to promote nuclear translocation. In the nucleus, the DNA binding domain directs dimerization on imperfect DNA palindromes known as simple glucocorticoid response elements (GREs) to transcriptionally activate genes including tyrosine amino transferase (TAT).

Primary hepatocytes were distributed in 96-well collagen coated plates and equilibrated in media (without hydrocortisone) for 6 hours. Compounds were tested at 6 concentrations (semi-log dilutions) and prepared in 0.2% DMSO in the presence of 50 nM dexamethasone or media. Hepatocytes in the presence of compound were incubated for 24 hours, washed in PBS and lysed for 30 minutes (30 μl lysis volume). The TAT enzyme assay was initiated by the addition of 170 μl TAT assay buffer (substrate) for 1 hour. The reaction was terminated by the addition of 30 μl 10N KOH and the 96-well plates incubated for a further 30 min at to allow formation of the aromatic aldehyde product, p-hydroxybenzaldehyde. Absorbance was read at 340 nM on a spectrophotometer.

Reagents: TAT assay buffer: 0.2 M $KH_2PO_4$ pH7.4 containing 5.4 mM L-tyrosine, 10.8 mM α-ketoglutaric acid and 0.06 mM Pyridoxal-5-phosphate monohydrate.

Figure 2A:
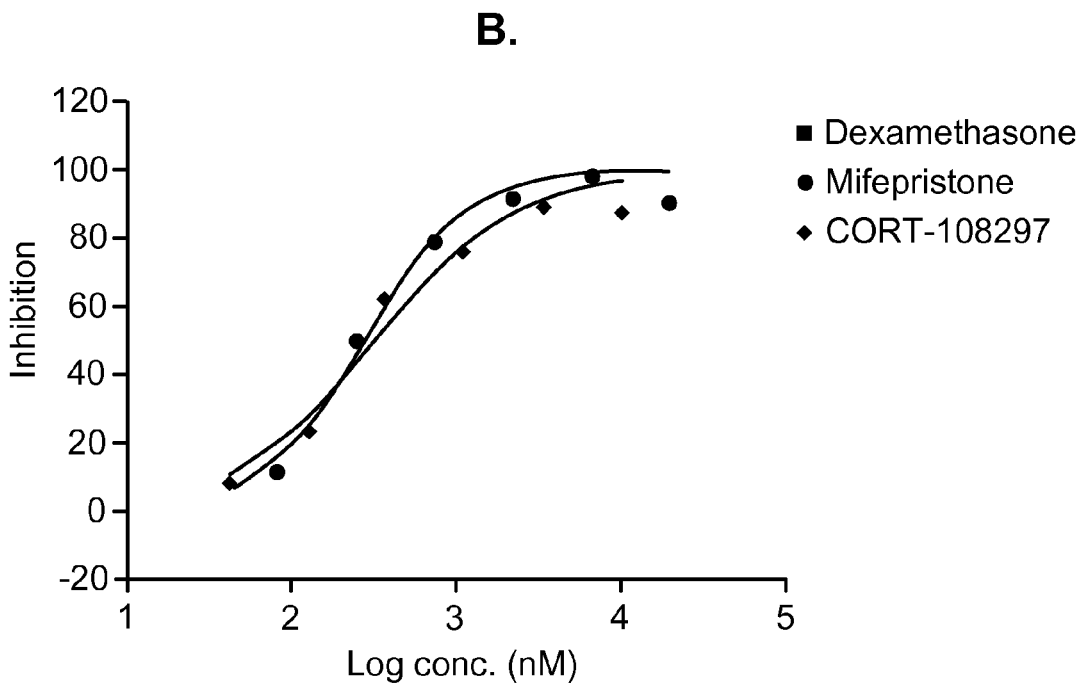
FIG. 2a shows that while dexamethasone promotes maximal transactivation (shown by inducing the expression of tyrosine amino transferase) at a concentration of about 100 nM (squares), CORT-108297 does not substantially promote transactivation (circles).

Dexamethasone was used to increase the expression of tyrosine amino transferase in human liver hepatocytes. FIG. 2a demonstrates that dexamethasone causes a dose dependent increase in TAT expression with maximal effect at a concentration of about 100 nM. In contrast, FIG. 2a demonstrates that the expression of tyrosine amino transferase does not increase above about 0% for all the concentrations of CORT-108297 assayed.

As depicted in FIG. 2b, both mifepristone and CORT-108297 inhibit the increased expression of tyrosine amino transferase caused by dexamethasone. As such, CORT-108297 is a full potent antagonist of GR induced transactivation.

Example 2

Glucocorticosteroid Transrepression Assay

This example demonstrates that the compositions of the present invention do not substantially inhibit glucocorticosteroid induced transrepression. Specifically, the compositions of the present invention do not substantially inhibit dexamethasone induced transrepression with regard to LPS activated TNFα release (NFκB responsive gene).

Human peripheral blood mononuclear cells were isolated and distributed in 96-well plates at a density of $2 \times 10^5$ cells/well in medium. Compounds were tested at 7 concentrations (semi-log dilutions) and prepared at 5× final assay concentration in 1.5% DMSO. Following a preincubation of 30 minutes with compounds the plates are then incubated in presence of 50 nM dexamethasone or media for 30 minutes. TNFα release was activated by overnight incubation with 10 ng/ml LPS. Human TNFα was measured using chemiluminescence detected on the SECTOR® Imager 6000 (Mesoscale). Dexamethasone was used to inhibit LPS activated TNFα release via the glucocorticoid receptor. Either mifepristone or CORT-108297 was added to block the inhibition of LPS activated TNFα release achieved by dexamethasone. In some cases, CORT-108297 was added in the absence of dexamethasone to determine if CORT-108297 inhibited LPS activated TNFα release.

FIG. 1a, shows that dexamethasone inhibits the release of TNFα activated by LPS, and maximal inhibition is achieved at nanomolar concentrations. FIG. 1b shows that mifepristone completely blocks this effect, while CORT-108297 only shows partial blockade at higher concentrations. As such, mifepristone is observed to fully reverse dexamethasone induced repression of LPS activated TNFα release. In contrast, CORT-108297 does not substantially inhibit dexamethasone induced transrepression.

FIG. 1a demonstrates that CORT-108297 partially inhibits LPS activated TNFα release, with a maximal 48% inhibition at micromolar concentrations. Thus, CORT-108297 is a weak partial agonist of GR induced transrepression. Also, CORT-108297 is observed to produce weak incomplete blockade of glucocorticosteroid-, e.g. dexamethasone, induced transrepression. When CORT-108297 is used in conjunction with an anti-inflammatory glucocorticosteroid, there is no substantial inhibition of the glucocorticsteroid's anti-inflammatory transrepression activity while there is inhibition of the glucocorticosteroid's side effects which are mediated by transactivation activity.

Example 3

Treatment of Male Patient with Arthritis

A 50 year-old male, weighing 175 pounds, presents to a physician with arthritis. The physician prescribes 2 mg of dexamethasone and 20 mg of CORT-108297:

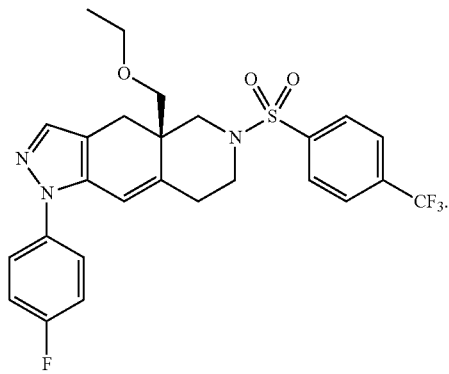 [SMILES: CCOC[C@]12Cc3cnn(-c4ccc(F)cc4)c3C=C1CCN(S(=O)(=O)c1ccc(C(F)(F)F)cc1)C2]

to be taken in combination for treatment of the arthritis.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of inhibiting glucocorticoid receptor-(GR) induced transactivation without substantially inhibiting GR induced transrepression, the method comprising contacting a GR with a composition comprising an anti-inflammatory glucocorticosteroid able to induce induce both GR transactivation and GR transrepression, and a GR modulator of Formula I:

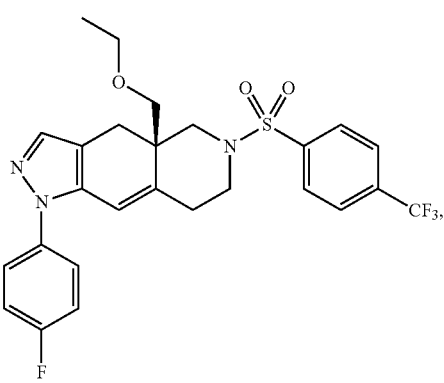 [SMILES: CCOC[C@]12Cc3cnn(-c4ccc(F)cc4)c3C=C1CCN(S(=O)(=O)c1ccc(C(F)(F)F)cc1)C2]

in an amount sufficient to inhibit GR induced transactivation without substantially inhibiting GR induced transrepression.

2. The method of claim 1, wherein the method further treats a disorder or condition selected from the group consisting of glaucoma, inflammatory diseases, rheumatoid arthritis, asthma and rhinitis, chronic obstructive pulmonary disease, allergies and autoimmune diseases.

3. The method of claim 1, wherein the method further reduces the side effects of glucocorticosteroid treatment.

4. The method of claim 3, wherein the side effects of glucocorticosteroid treatment are selected from the group consisting of weight gain, glaucoma, fluid retention, increased blood pressure, mood swings, cataracts, high blood sugar, diabetes, infection, loss of calcium from bones, osteoporosis, menstrual irregularities, fat redistribution, growth retardation and cushingoid appearance.

5. The method of claim 1, wherein the anti-inflammatory glucocorticosteroid is selected from the group consisting of alclometasone, beclometasone, betamethasone, budesonide, ciclesonide, clobetasol, clocortolone, cortexolone, cortisol, cortisporin, cortivazol, deflazacort, deprodone, desonide, dexamethasone, difluprednate, fludroxycortide, flunisolide, fluocinolone, fluocinonide, fluocortolone, fluorometholone, fluticasone, halcinonide, halometasone, halopredone, hydrocortisone, loteprednol, meprednisone, methylprednisolone, mometasone, naflocort, 19-nordeoxycorticosterone, 19-norprogesterone, otobiotic, oxazacort, paramethasone, prednicarbate, prednisolone, prednisone, prednylidene, proctosedyl, rimexolone, tobradex, triamcinolone, trimexolone, ulobetasol, 11β-(4-dimethylaminoethoxyphenyl)-17α-propynyl-17β-hydroxy-4,9estradien-3-one (RU009), and 17β-hydroxy-17α-19-(4-methylphenyl)androsta-4,9(11)-dien-3-one (RU044).

6. A composition comprising: an anti-inflammatory glucocorticosteroid; and a glucocorticoid receptor (GR) modulator of Formula I:

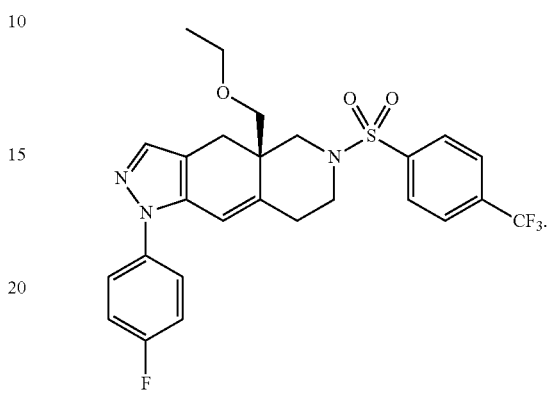

7. The composition of claim 6, wherein the anti-inflammatory glucocorticosteroid is selected from the group consisting of alclometasone, beclometasone, betamethasone, budesonide, ciclesonide, clobetasol, clocortolone, cortexolone, cortisol, cortisporin, cortivazol, deflazacort, deprodone, desonide, dexamethasone, difluprednate, fludroxycortide, flunisolide, fluocinolone, fluocinonide, fluocortolone, fluorometholone, fluticasone, halcinonide, halometasone, halopredone, hydrocortisone, loteprednol, meprednisone, methylprednisolone, mometasone, naflocort, 19-nordeoxycorticosterone, 19-norprogesterone, otobiotic, oxazacort, paramethasone, prednicarbate, prednisolone, prednisone, prednylidene, proctosedyl, rimexolone, tobradex, triamcinolone, trimexolone, ulobetasol, 11β-(4-dimethylaminoethoxyphenyl)-17α-propynyl-17β-hydroxy-4, 9estradien-3-one (RU009), and 17β-hydroxy-17α-19-(4-methylphenyl)androsta-4,9(11)-dien-3-one (RU044).

8. The composition of claim 6, further comprising a pharmaceutically acceptable excipient.

* * * * *